United States Patent [19]

Katdare

[11] Patent Number: 4,898,736

[45] Date of Patent: Feb. 6, 1990

[54] METHOD FOR TABLET PREPARATION

[75] Inventor: Ashok V. Katdare, Norristown, Pa.

[73] Assignee: Merck & Co., Inc., Rayway, N.J.

[21] Appl. No.: 166,078

[22] Filed: Mar. 9, 1988

[51] Int. Cl.⁴ ............................................. A61K 9/20
[52] U.S. Cl. .................................. 424/465; 424/469; 424/470
[58] Field of Search ............................... 424/464, 465

[56] References Cited

U.S. PATENT DOCUMENTS

| | | | |
|---|---|---|---|
| 4,489,026 | 12/1984 | Yalkowsky | 424/465 |
| 4,710,504 | 12/1987 | Baldwin et al. | 514/267 |
| 4,719,228 | 1/1988 | Rawlins | 424/464 |

OTHER PUBLICATIONS

Cox, J. Pharm. Pharmaco 1968, 20(3), 238–239.

Primary Examiner—Ellis P. Robinson
Assistant Examiner—Leon R. Howe
Attorney, Agent, or Firm—William H. Nicholson; Joseph F. DiPrima

[57] ABSTRACT

Dose uniformity in formulations of highly potent drugs may be achieved by distributing a solution of the active ingredient over a directly compressible tableting vehicle with subsequent evaporation of the solvent, followed by tableting.

2 Claims, No Drawings

METHOD FOR TABLET PREPARATION

BACKGROUND OF THE INVENTION

The pharmaceutical industry employs many methods for the preparation of granulations that subsequently are converted to finished dosage forms. Among these are: wet granulation; dry granulation; and direct compression. In any of these methods it is difficult to ensure uniform distribution of the active ingredient throughout the excipients to provide a homogeneous tablet. This is especially true with an extremely active medicament wherein the unit dose of drug may be very small.

The present invention provides a process that ensures dose uniformity in low dose tablet formulations while keeping unit operations to a minimum.

DETAILED DESCRIPTION OF THE INVENTION

This invention is concerned with a novel process for the preparation of uniform low dose tablets which comprise the steps of: dissolving the drug in a solvent; distributing the solution over a directly compressible tableting vehicle; evaporating the solvent; adding a lubricant and other excipients if desired; and compressing the powder mixture into tablets.

The novel process is especially useful for formulating drugs of which the unit dose is about 50 $\mu$g to 1000 $\mu$g.

The solvent typically is one in which the drug is readily soluble and which can be easily evaporated such as ethanol, methanol, acetone, tetrahydrofuran, or the like.

The directly compressible tableting vehicle is one such as processed forms of dicalcium phosphate dihydrate, compressible sucrose, lactose, mannitol, microcrystalline cellulose, other celluloses, or modified starches.

As lubricant there can be used any lubricant known in the art, such as magnesium stearate, calcium stearate, stearic acid, glyceryl behenate, or the like.

Other excipients well known in the art may be added as fillers, such as colloidal silicon dioxide, calcium sulfate, or the like.

The amount of solvent used to introduce the active ingredient should be held to a minimum so that evaporation and removal of it is facilitated.

EXAMPLE 1

Procedure for Manufacturing 50 $\mu$g Potency Tablets of (2S, 12bS)-1',3'-dimethylspiro-(1,3,4,6,7,12b-hexahydrobenzo[b]furo[2,3-a]quinolizin)-2,4'-(5',6'-dihydro-1'H-pyrimidine-2'(3'H)-one).

|  |  | Per 6000 Tablets |
| --- | --- | --- |
| Active ingredient (anhydrous) | 50 $\mu$g | 0.300 gm |
| Microcrystalline cellulose, NF | 75.9 mg | 455.0 gm |
| Pregelatinized Starch, NF | 23.0 mg | 138.0 gm |
| Magnesium stearate impalpable powder, NF | 1.0 mg | 6.0 gm |

The active ingredient was dissolved in 6 ml of anhydrous ethanol (SD3A) and added to microcrystalline cellulose contained in a blender bowl while being mixed at 40-50 rpm. The active ingredient was rinsed in with 2×2 ml portions of anhydrous ethanol. Mixing was continued for 6 minutes at 40 rpm. The microcrystalline cellulose/active ingredient (after most or all of the ethanol had evaporated) was passed through a #30 (U.S. Standard) screen and dried until the odor of alcohol had disappeared. The pregelatinized starch was added by passing it through a #30 (U.S. Standard) screen. The powder mix was mixed in a blender for 7 minutes at 40 rpm. Magnesium stearate was added by passing it through a #60 (U.S. Standard) screen and mixing was continued for an additional 3 minutes at 40 rpm.

The lubricated mixture was compressed using an 8/32' hexagonal tablet tooling to provide a tablet of 50 $\mu$g of active ingredient.

EXAMPLE 2

Procedure for Manufacturing 100 $\mu$g Potency Tablets of (2S,12bS)-1',3'-dimethylspiro-(1,3,4,6,7,12b-hexahydrobenzo[b]furo[2,3-a]quinolizin)-2,4'-(5',6'-dihydro-1'H-pyrimidine-2'(3'H)-one).

|  | Per 5000 Tablets |
| --- | --- |
| Active ingredient (anhydrous) | 600 mg |
| Microcrystalline cellulose, NF | 379.5 g |
| Pregelatinized starch, NF | 115 g |
| Magnesium stearate impalpable powder, NF | 5.0 g |

Tablets were prepared using substantially the same procedure as described in Example 1 using 15 ml of ethanol and 2×5 ml portions of ethanol as washes.

EXAMPLE 3

Uniformity Test

Tablets are dissolved and diluted with 25% acetonitrile/75% water solution. The samples are assayed by reversed-phase HPLC at 35° C. with UV detection (210 nm) utilizing a phenyl column with a mobile phase of acetonitrile:aqueous phosphate solution (adjusted to pH 30).

Actual results, typical of the uniformity achieved are as follows:

| | mg/Tablet in | |
| --- | --- | --- |
| 0.05 mg Tablets | 0.1 mg Tablets | 1 mg Tablets |
| 0.0494 | 0.0968 | 1.0194 |
| 0.0501 | 0.0939 | 1.0094 |
| 0.0490 | 0.0949 | 0.9953 |
| 0.0494 | 0.0956 | 1.0007 |
| 0.0503 | 0.0954 | 1.0086 |
| 0.0491 | 0.0968 | 1.0107 |
| 0.0494 | 0.0950 | 1.0244 |
| 0.0504 | 0.0972 | 1.0265 |
| 0.0497 | 0.0961 | 1.0202 |
| 0.0495 | 0.0953 | 1.0394 |
| MEAN 0.0496 | 0.0957 | 1.0155 |
| RSD 0.9781% | 1.073% | 1.2897% |

What is claimed is:

1. A process for the preparation of low dose (2S,12bS)-1',3'-dimethylspiro(1,3,4,6,7,12b-hexahydrobenzo-[2,3-a]quinolizin)-2,4'-(5',6'-dihydro-1'H-pyrimidine-2'(3'H)-one) tablets comprising the steps: dissolving (2S,12bS)-1',3'-dimethylspiro(1,3,4,6,7,12b-hexahydrobenzo]2,3-a]quinolizin)-2,4'-(5',6'-dihydro-1'H-pyrimidine-2'(3'H)-one) in a suitable easily evaporated solvent; mixing the solution with a directly compressible powder tableting vehicle; evaporating the solvent; adding a lubricant and other excipients if desired; and compressing the mixture into tablets.

2. The process of claim 1 wherein the easily evaporated solvent is ethanol, methanol, acetone or tetrahydrofuran and the low dose is about 50-1000 $\mu$g.

* * * * *